United States Patent
Deirmendjian et al.

[19]

[11] Patent Number: 5,899,870
[45] Date of Patent: May 4, 1999

[54] THUMB SPLINT

[76] Inventors: Gary Kara Deirmendjian, 5/529-533 Church Street, North Parramatta, New South Wales 2151; Eugene Sherry, 25 Ridge Street, Gordon, New South Wales, 2072, both of Australia

[21] Appl. No.: 08/709,749

[22] Filed: Sep. 9, 1996

[51] Int. Cl.[6] .............................. A61F 5/00; A61F 13/00
[52] U.S. Cl. .............................. 602/21; 602/62; 128/880
[58] Field of Search .................... 602/20–22, 62–64, 602/75, 5; 128/878–880; 473/422, 458, 464, 518, 553

[56] References Cited

U.S. PATENT DOCUMENTS

| | | | |
|---|---|---|---|
| 1,315,035 | 2/1919 | Post | 602/22 X |
| 1,990,384 | 2/1935 | Klohs | 128/880 |
| 3,050,053 | 8/1962 | Peckham | 602/5 |
| 3,497,218 | 2/1970 | Johnston | 473/458 |
| 4,040,632 | 8/1977 | Pawl | 473/464 X |
| 4,632,105 | 12/1986 | Barlow | 602/64 |
| 4,796,306 | 1/1989 | Mitchell | 2/160 |
| 4,953,568 | 9/1990 | Thiesler | 128/880 X |
| 5,356,371 | 10/1994 | Hubbard | 602/22 |
| 5,447,490 | 9/1995 | Fula | 602/21 X |
| 5,466,215 | 11/1995 | Larr et al. | 602/64 X |
| 5,515,870 | 5/1996 | Zilber | 128/880 X |

*Primary Examiner*—Richard J. Apley
*Assistant Examiner*—Denise Pothier
*Attorney, Agent, or Firm*—Oppenheimer Wolff & Donnelly LLP

[57] ABSTRACT

A thumb support (1) including a thumb engaging portion (3) and an anchoring portion (5). The thumb engaging portion (3) is attached to the anchoring portion (5) by means a first elastically extensible strap (7), such that the thumb is resiliently biased towards a preselected healing position. In a preferred embodiment, a second elastically extensible strap (9) is included which provides additional support.

4 Claims, 2 Drawing Sheets

THUMB SPLINT

BACKGROUND OF THE INVENTION

The present invention relates to an apparatus for maintaining a user's thumb in a predetermined healing position.

Injuries to the thumb and adjacent muscles and ligaments commonly occur during many sports, including various types of football, basketball, cricket, baseball, and snow skiing. Such injuries can also occur during day-to-day activities through accidental falls or other mishaps.

The majority of these injuries involve damage to the ulnar collateral ligament of the metacarpal phalangeal joint (MCP joint) of the thumb, and may vary from minor sprains through to partial and complete tearing of the ligament. A complete tear requires immediate surgery, whilst other types of injuries may heal by themselves given adequate time and rest.

After injury or surgery, it is necessary to minimise strain on the ligament, thereby to promote faster and better healing. In the past, this has generally been achieved by means of standard bandages or taping. However, such measures require expert application, and moreover provide a relatively static support by binding the thumb against the adjacent hand.

There are available some splint and brace devices which are designed to immobilise the thumb in a particular position. One type utilises metallic or plastics splints within an elastic lycra or neoprene casing. In use, the splints lie along the outside of the thumb to maintain it in a particular position. Other types of splints are formed from rigid plastics materials designed to envelope the thumb.

A disadvantage of all these supports is that they tend to be cumbersome, and difficult to remove and apply, particularly if the wearer is in pain. Due to their passive nature, they do not enable use of the thumb in its usual capacity, and are not therefore able to be used as an injury prevention device. Furthermore, such splints generally fail to maintain the thumb in an optimal healing position as they often fail to position the thumb correctly.

SUMMARY OF THE INVENTION

It is an object of the invention to overcome or at least substantially ameliorate one or more of the disadvantages of the prior art.

Accordingly, in a first aspect, the invention provides a thumb support including a thumb engaging portion and an anchoring portion, wherein the thumb engaging portion is attached to said anchoring portion by means of an elastically extensible strap, such that the thumb is resiliently biased towards a preselected healing position.

Preferably, the elastically extensible strap extends from the thumb engaging portion at a point adjacent the pad of the thumb to a point on the anchoring portion adjacent the back of the hand.

It is also preferable that the elastically extensible strap engages the web of the hand between the thumb and the adjacent index finger.

Desirably, the elastically extensible strap exerts pressure on the web, thereby to move the thumb generally towards the palm of the hand.

In a preferred embodiment, the anchoring portion takes the form of a cuff encircling the wrist of the user.

In another preferred embodiment, the elastically extensible strap is releasably attachable to one or both of the anchoring and thumb engaging portions. Preferably, the releasable attachment is achieved by means of a loop/hook fastener, typically of the type sold under the trade name VELCRO®.

In one preferred embodiment, the anchoring portion and the thumb engaging portion are integrally formed, and are formed from a plastics material such as neoprene.

BRIEF DESCRIPTION OF THE DRAWINGS

A preferred embodiment of the invention will now be described, by way of example only, with reference to the accompanying drawings in which.

DESCRIPTION OF PREFERRED EMBODIMENT

Figure 1:
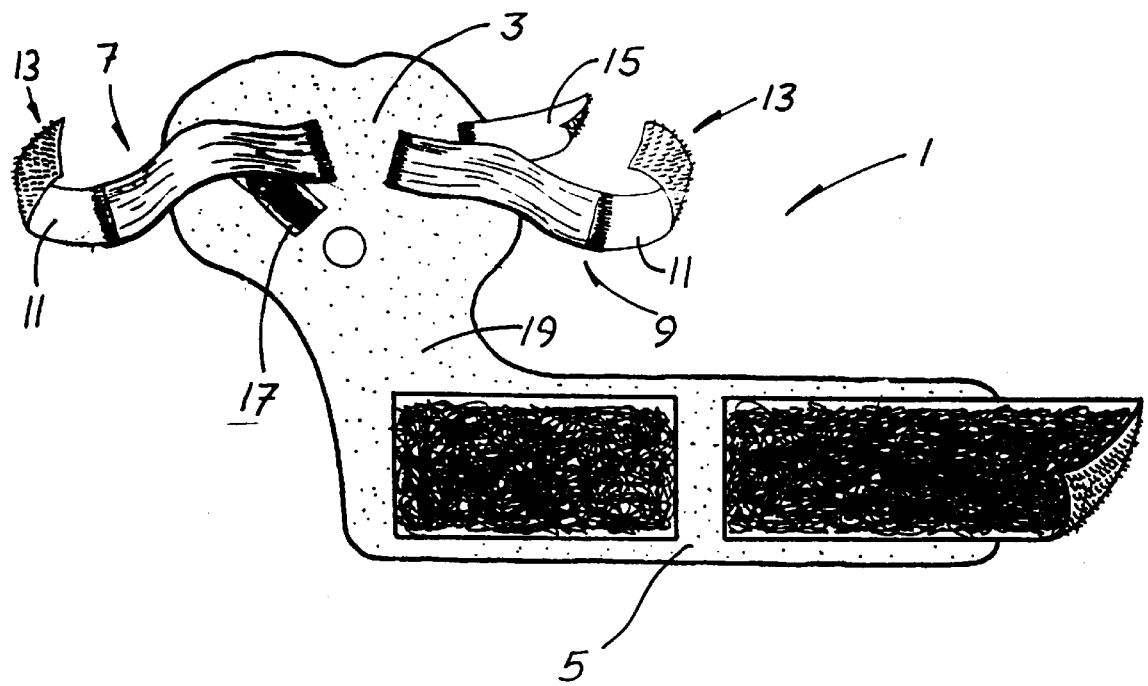
FIG. 1 is a plan view of the outer surface of a thumb support according to the invention.

Referring to the drawings, a thumb support 1 includes a thumb engaging portion 3 and an anchoring portion in the form of a cuff 5. First and second elastically extensible straps 7 and 9 extend from thumb engaging portion 3, each terminating in an inextensible portion 11 including an array of nylon hooks 13. In the embodiment shown, the thumb engaging portion 3 and the cuff 5 are linked by a bridging portion 19, although this is not essential.

A thumb strap 15 extends from an edge of the thumb engaging portion and includes an array of nylon hooks for engagement with a series of loops formed on pad 17.

The thumb support is formed from neoprene, although other suitable materials may be chosen depending upon the actual circumstances of use.

Figure 2:
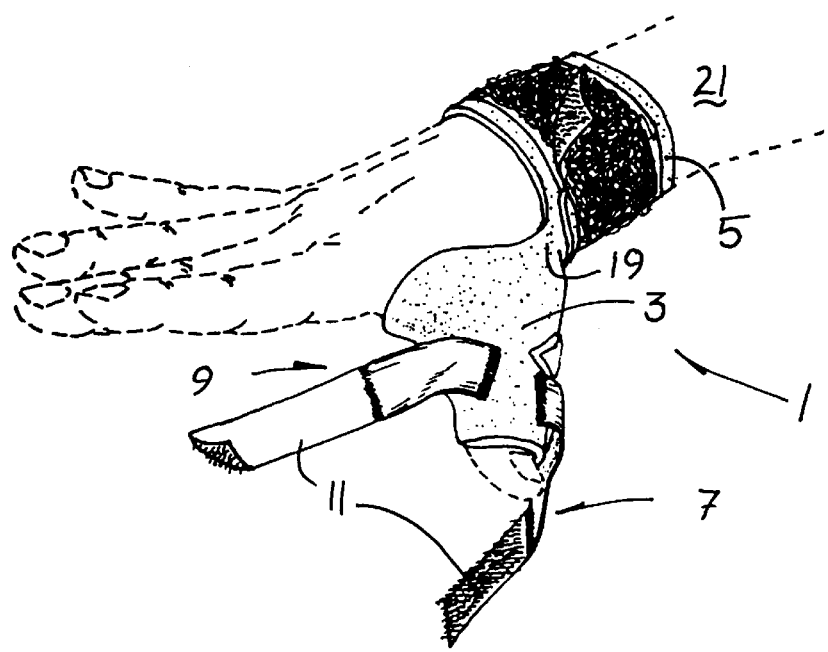
FIG. 2 is a perspective view of the thumb support shown in FIG. 1, being partially installed to a user's hand.

The steps required to apply the thumb support to a user's handle will now be described in detail. Turning to FIG. 2, initially, the cuff 5 is looped around the user's wrist 21 in an overlapping fashion and secured firmly by means of hook and loop fastening. The thumb engaging portion 3 is positioned so that it extends along the outer surface of the user's thumb, and is then secured to the thumb by means of the hook and loop fastening between thumb strap 15 and pad 17.

Figure 3:
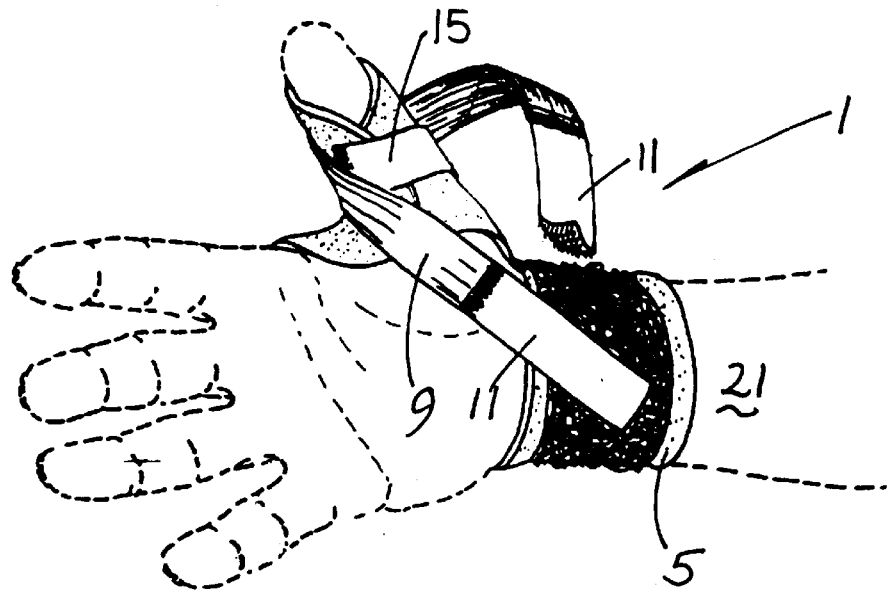
FIG. 3 is a different perspective view of the device shown in FIGS. 1 and 2 with installation nearly completed.

Turning to FIG. 3, second elastically extensible strap 9 is then drawn around the thumb on the side adjacent the index figure and attached to the cuff 5 by means of hook and loop fastening. The effect on the thumb of the wearer may be adjusted to suit the circumstances by altering the tension on the second elastically extensible strap 9 before attaching it to the cuff 5.

Figure 4:
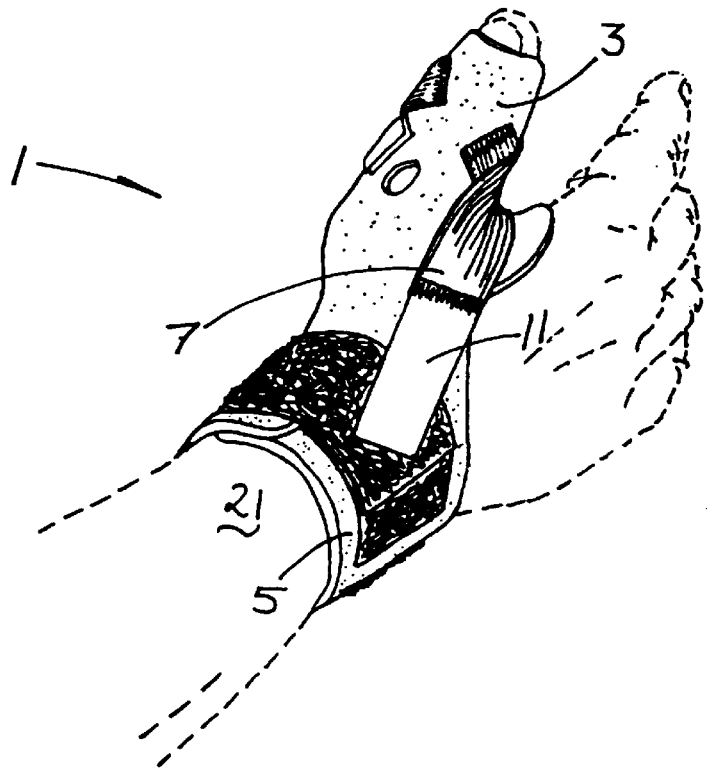
FIG. 4 is yet another perspective view of the device shown in FIGS. 1, 2 and 3 in use.

Turning to FIG. 4, the first elastically extensible strap 7 is drawn around the thumb in the opposite direction to pass between the thumb and index finger, and is secured to the cuff 5 adjacent the back of the wearer's wrist by hook and loop fastening. The first elastically extensible strap 7 is positioned so that it engages the thumb engaging portion 3 where it covers the web of the user's hand formed between the thumb and index finger. By adjusting the tension of the first elastically extensible strap 7, the amount of pressure exerted on the web, and thereby the force acting on the thumb to move it towards the healing position, is adjustable to suit the needs of the wearer.

In use, the thumb support dynamically restricts movement of the thumb away from the healing position. More specifically, extension and abduction of the thumb is resiliently opposed by the elastically extensible straps 7 and 9, and the first elastically extensible strap 7 in particular. The elastically extensible straps also tend to roll the user's thumb generally towards the palm, which once again promotes rapid and correct healing of the damaged ligament.

Although the thumb support of the invention has been designed specifically to promote protection of the ulnar collateral ligament during healing, it is also an effective preventative measure. By wearing the thumb support during sport or other activities where injury to the ligament is likely, the invention provides an additional degree of protection which will prevent or reduce the severity of any injury at the first instance. Unlike prior art devices, the present invention allows the thumb to retain some degree of movement.

Whilst hook and loop fasteners have been used extensively in the preferred embodiment due to their convenience and speed of attachment, other fastening means such as clips, buttons, or buckles may also be used according to the user's preference. Similarly, materials other than neoprene may be used depending upon the application. For example, a relatively water proof plastics material may be utilised where the thumb support is likely to get wet.

In other embodiments, the anchoring portion may be positioned closer to the user's elbow, or even on the hand itself in some circumstances. It may also be formed separately from the thumb engaging portion or the two may together form part of a glove arrangement.

The present invention provides a means of dynamically biasing the thumb of a user towards a healing position, thereby allowing faster and better healing of the ulnar collateral ligament. Unlike prior art devices, the thumb support of the present invention is relatively easy to remove and apply even using one hand. In a preferred embodiment, the wrap around nature of the both the cuff and the thumb engaging portion ensure that the device may be positioned with little pain to the user. Furthermore, because the support allows for resiliently opposed movement of the thumb, the thumb may be used in its usual capacity, which gives the present invention the advantage of being useable as an injury prevention device. The present invention therefore represents a commercially significant improvement over prior art thumb supports.

Although the invention has been described with reference to a particular example, it will be appreciated that the invention may be embodied in many other forms.

We claim:

1. A thumb support including a thumb engaging portion and an anchoring portion, wherein the thumb engaging portion is attached to said anchoring portion by a first elastically extensible strap, said first elastically extensible strap being configured to resiliently adduct the thumb, wherein the first elastically extensible strap extends from the thumb engaging portion at a point adjacent the pad of the thumb to a point on the anchoring portion adjacent the back of the hand, the thumb support further including a second elastically extensible strap which, in use, extends from the thumb engaging portion at a point adjacent the pad of the thumb to a point on the anchoring portion adjacent the inner wrist.

2. A thumb support according to claim 1 wherein either or both of the elastically extensible straps is releasably attachable to one or both of said anchoring and thumb engaging portions.

3. A thumb support according to claim 2 wherein either or both of said elastically extensible straps is attachable by means of hook and loop fastening.

4. A thumb support including a thumb engaging portion and an anchoring portion, wherein the thumb engaging portion is attached to said anchoring portion by a first elastically extensible strap, said first elastically extensible strap being configured to resiliently adduct the thumb, wherein the first elastically extensible strap extends from the thumb engaging portion at a point adjacent the pad of the thumb to a point on the anchoring portion adjacent the back of the hand, the thumb support being configured such that, in use, the first elastically extensible strap engages the web of the hand between the thumb and the adjacent index finger thereby moving the thumb generally towards the palm of the hand.

\* \* \* \* \*